(12) United States Patent
Nakamura et al.

(10) Patent No.: US 9,618,563 B2
(45) Date of Patent: Apr. 11, 2017

(54) SEMICONDUCTOR DEVICE INSPECTION DEVICE AND SEMICONDUCTOR DEVICE INSPECTION METHOD

(71) Applicant: HAMAMATSU PHOTONICS K.K., Hamamatsu-shi, Shizuoka (JP)

(72) Inventors: Tomonori Nakamura, Hamamatsu (JP); Mitsunori Nishizawa, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 63 days.

(21) Appl. No.: 14/764,327

(22) PCT Filed: Jan. 30, 2014

(86) PCT No.: PCT/JP2014/052145
§ 371 (c)(1),
(2) Date: Jul. 29, 2015

(87) PCT Pub. No.: WO2014/119675
PCT Pub. Date: Aug. 7, 2014

(65) Prior Publication Data
US 2015/0369755 A1 Dec. 24, 2015

(30) Foreign Application Priority Data

Feb. 1, 2013 (JP) .................................. 2013-018683

(51) Int. Cl.
*G01N 21/00* (2006.01)
*G01R 31/265* (2006.01)
(Continued)

(52) U.S. Cl.
CPC ..... *G01R 31/2656* (2013.01); *G01N 21/9501* (2013.01); *G01R 23/16* (2013.01);
(Continued)

(58) Field of Classification Search
CPC ..... G01N 21/9501; G01N 21/00; G01R 23/16
(Continued)

(56) References Cited

U.S. PATENT DOCUMENTS

| 5,767,688 A | 6/1998 | Takahashi et al. |
| 5,905,577 A | 5/1999 | Wilsher et al. |

(Continued)

FOREIGN PATENT DOCUMENTS

| JP | H01-169862 A | 7/1989 |
| JP | H05-013522 A | 1/1993 |

(Continued)

*Primary Examiner* — Roy M Punnoose
(74) *Attorney, Agent, or Firm* — Drinker Biddle and Reath LLP

(57) ABSTRACT

A semiconductor device inspection system includes a laser light source for generating light to be irradiated a semiconductor device, an optical sensor for detecting the light reflected by the semiconductor device and outputting the detection signal, a tester unit for applying a operating signal to the semiconductor device, an electricity measurement unit to which the detection signal is input, an electricity measurement unit to which the detection signal and the operating signal are selectively input, and a switching unit having a detection signal terminal and a operating signal terminal. The switching unit inputs the detection signal to the electricity measurement unit by connecting a connection section to the detection signal terminal and inputs the operating signal by connecting the connection section to the operating signal terminal.

12 Claims, 5 Drawing Sheets

(51) Int. Cl.
*G01R 31/311* (2006.01)
*H01L 21/66* (2006.01)
*G01N 21/95* (2006.01)
*G01R 23/16* (2006.01)

(52) U.S. Cl.
CPC .......... *G01R 31/311* (2013.01); *H01L 22/12* (2013.01); *G01N 2201/12* (2013.01)

(58) Field of Classification Search
USPC ..................................................... 356/237.5
See application file for complete search history.

(56) References Cited

U.S. PATENT DOCUMENTS

| | | | |
|---|---|---|---|
| 6,232,765 | B1 | 5/2001 | Takeuchi et al. |
| 6,252,222 | B1 | 6/2001 | Kasapi et al. |
| 6,976,234 | B2 * | 12/2005 | Kasapi ............. G01R 31/31937 324/501 |
| 7,659,981 | B2 | 2/2010 | Lo et al. |
| 9,099,350 | B2 | 8/2015 | Nakamura et al. |
| 2007/0046301 | A1 | 3/2007 | Kasapi |
| 2010/0039131 | A1 | 2/2010 | Kasapi |
| 2012/0307249 | A1 | 12/2012 | Nakamura et al. |
| 2015/0130474 | A1 | 5/2015 | Nakamura et al. |
| 2015/0276865 | A1 | 10/2015 | Nakamura |
| 2015/0309115 | A1 | 10/2015 | Nakamura et al. |
| 2015/0369755 | A1 | 12/2015 | Nakamura et al. |

FOREIGN PATENT DOCUMENTS

| | | |
|---|---|---|
| JP | H05-047883 A | 2/1993 |
| JP | H05-164788 A | 6/1993 |
| JP | H06-201803 | 7/1994 |
| JP | H07-134147 A | 5/1995 |
| JP | H08-211131 A | 8/1996 |
| JP | 2001-255354 A | 9/2001 |
| JP | 2007-064975 A | 3/2007 |
| JP | 2010-271307 A | 12/2010 |
| KR | 101996003504 | 10/1996 |

* cited by examiner

SEMICONDUCTOR DEVICE INSPECTION DEVICE AND SEMICONDUCTOR DEVICE INSPECTION METHOD

TECHNICAL FIELD

The present invention relates to a semiconductor device inspection system and a semiconductor device inspection method.

BACKGROUND ART

As a technology of inspecting an integrated circuit, an optical probing technologies referred to as electro optical probing (EOP) and electro-optical frequency mapping (EOFM) are known. In such optical probing technologies, light emitted from a light source is irradiated to an integrated circuit, and the light reflected by the integrated circuit is detected by an optical sensor to acquire a detection signal. Then, in the acquired detection signal, a desired frequency is selected, and amplitude energy thereof is displayed as time progression or two-dimensional mapping is displayed. Accordingly, a position of the circuit operated at a desired frequency can be specified.

CITATION LIST

Patent Literature

[Patent Literature 1] Japanese Unexamined Patent Application, First Publication No. 2007-64975
[Patent Literature 2] Japanese Unexamined Patent Application, First Publication No. 2001-255354
[Patent Literature 3] Japanese Unexamined Patent Application, First Publication No. 2010-271307

SUMMARY OF INVENTION

Technical Problem

The above-mentioned optical probing technology is extremely effective technology because a portion in which a failure occurs, a cause of a failure, and so on, in a semiconductor device such as an integrated circuit can be specified.

Here, the present invention is directed to provide a semiconductor device inspection system and a semiconductor device inspection method that are capable of efficiently and precisely performing inspection of a semiconductor device.

Solution to Problem

A semiconductor device inspection system according to an aspect of the present invention includes a light generating unit for generating light to be irradiated a semiconductor device serving as a device under test; a light detection unit for detecting the light reflected by the semiconductor device and outputting a detection signal when the light generated from the light generating unit is irradiated to the semiconductor device; an operating signal application unit for applying the operating signal that operates the semiconductor device to the semiconductor device; a first electricity measurement unit to which the detection signal is input; a second electricity measurement unit to which the detection signal and the operating signal are selectively input; and a switching unit having a first signal terminal electrically coupled to the light detection unit, a second signal terminal electrically coupled to the operating signal application unit, and a connection section having one end electrically coupled to the second electricity measurement unit, wherein the switching unit inputs the detection signal to the second electricity measurement unit by connecting the other end of the connection section to the first signal terminal, and inputs the operating signal to the second electricity measurement unit by connecting the other end of the connection section to the second signal terminal.

In the semiconductor device inspection system, when the switching unit sets an access point of a connection section as the first signal terminal, digital signals in two frequencies can be simultaneously measured using the first and second electricity measurement units. That is, inspection of the semiconductor device can be efficiently performed. In addition, when the switching unit sets the access point of the connection section as the second signal terminal, since the detection signal is input to the first electricity measurement unit and the operating signal is input to the second electricity measurement unit, a phase difference can be calculated from the phase of the detection signal and the phase of the operating signal, and a portion in which a failure occurs and a cause of the failure can be specified according to the phase difference. That is, inspection of the semiconductor device can be precisely performed. Accordingly, according to the semiconductor device inspection system, inspection of the semiconductor device can be efficiently and precisely performed.

In the semiconductor device inspection system according to the aspect of the present invention, a signal attenuation unit installed between the first electricity measurement unit and the first signal terminal and for attenuating an electrical signal flowing in a direction from the first signal terminal toward the first electricity measurement unit may be further provided. According to the configuration, when the switching unit switches connection of the other end from the first signal terminal to the second signal terminal, the detection signal flowing backward from the first signal terminal toward the first electricity measurement unit and the operating signal flowing from the first signal terminal toward the first electricity measurement unit can be appropriately attenuated. Accordingly, input of a noise signal to the first electricity measurement unit can be prevented, and the phase difference between the detection signal and the operating signal can be precisely calculated.

In the semiconductor device inspection system according to the aspect of the present invention, the signal attenuation unit may have an amplifier for amplifying an electrical signal from the light detection unit toward the first signal terminal, and attenuating an electrical signal from the first signal terminal toward the first electricity measurement unit. In addition, the signal attenuation unit may have an amplifier for amplifying an electrical signal from the light detection unit toward the first signal terminal, and an attenuator for attenuating an electrical signal from the light detection unit toward the first signal terminal and an electrical signal from the first signal terminal toward the first electricity measurement unit. In addition, the signal attenuation unit may have an electrical resistor electrically coupled to the ground, the switching unit may have an attenuation switching unit electrically coupled to the electrical resistor, and the switching unit may electrically couple the attenuation switching unit to the first signal terminal when the other end of the connection section is connected to the second signal terminal. In addition, the signal attenuation unit may have an electrical resistor electrically coupled to the ground, the switching unit may further have a third signal terminal electrically coupled to the electrical resistor, a fourth signal terminal electrically coupled to the light detection unit, and an intermediate connection section having one end electrically coupled to the first signal terminal, and the switching unit may connect the intermediate connection section to the fourth signal terminal when the other end of the connection section is connected to the first signal terminal, and connect the intermediate connection section to the third signal terminal when the other end of the connection section is connected to the second signal terminal. According to the above-mentioned configuration, input of the noise signal to the first electricity measurement unit can be prevented, and the phase difference between the detection signal and the operating signal can be more precisely calculated.

In the semiconductor device inspection system according to the embodiment of the present invention, the first electricity measurement unit and the second electricity measurement unit may be a first spectrum analysis unit and a second spectrum analysis unit for measuring amplitudes of components of a complex wave.

In the semiconductor device inspection system according to the aspect of the present invention, a signal synchronization unit for synchronizing a frequency and a phase of a base signal that operates the first spectrum analysis unit with a frequency and a phase of a base signal that operates the second spectrum analysis unit when the switching unit connects the other end to the second signal terminal may be further provided. As the frequency and the phase of the base signal are synthesized between the spectrum analysis units, since overlapping of the phase difference due to operations of the spectrum analysis units can be prevented, the phase difference between the detection signal and the operating signal can be precisely calculated.

In the semiconductor device inspection system according to the aspect of the present invention, the first electricity measurement unit may be a spectrum analysis unit for measuring amplitudes of components of a complex wave, and the second electricity measurement unit is a lock-in amplification unit.

A semiconductor device inspection method according to an aspect of the present invention includes a light generation step of generating light irradiated to a semiconductor device serving as a device under test; a light detection step of detecting the light reflected by the semiconductor device when the light generated in the light generation step is irradiated to the semiconductor device, and outputting the detection signal; an operating signal application step of applying an operating signal that operates the semiconductor device to the semiconductor device; a first measurement step of inputting the detection signal to a first electricity measurement unit; and a second measurement step of selectively inputting the detection signal and the operating signal to a second electricity measurement unit. Even in the semiconductor device inspection method, for the same reasons as in the above-mentioned semiconductor device inspection system, inspection of the semiconductor device can be efficiently and precisely performed.

In the semiconductor device inspection method according to the aspect of the present invention, in the second measurement step, the operating signal may be input to the second electricity measurement unit after the detection signal is input to the second electricity measurement unit. The detection signals in the two frequencies can be measured by the first and second electricity measurement units to efficiently specify an abnormal frequency, and then a portion in which a failure occurs, a cause of the failure, and so on can be precisely specified from the phase difference between the detection signal and the operating signal.

In the semiconductor device inspection method according to the aspect of the present invention, in the second measurement step, the detection signal may be input to the second electricity measurement unit after the operating signal is input to the second electricity measurement unit. The portion in which the failure occurs and the cause of the failure can be specified from the phase difference between the detection signal and the operating signal, and processing such as removal of noises can be performed.

Advantageous Effects of Invention

According to an aspect of the present invention, it is possible to provide a semiconductor device inspection system and a semiconductor device inspection method that are capable of efficiently and precisely performing inspection of a semiconductor device.

DESCRIPTION OF EMBODIMENTS

Figure 1:
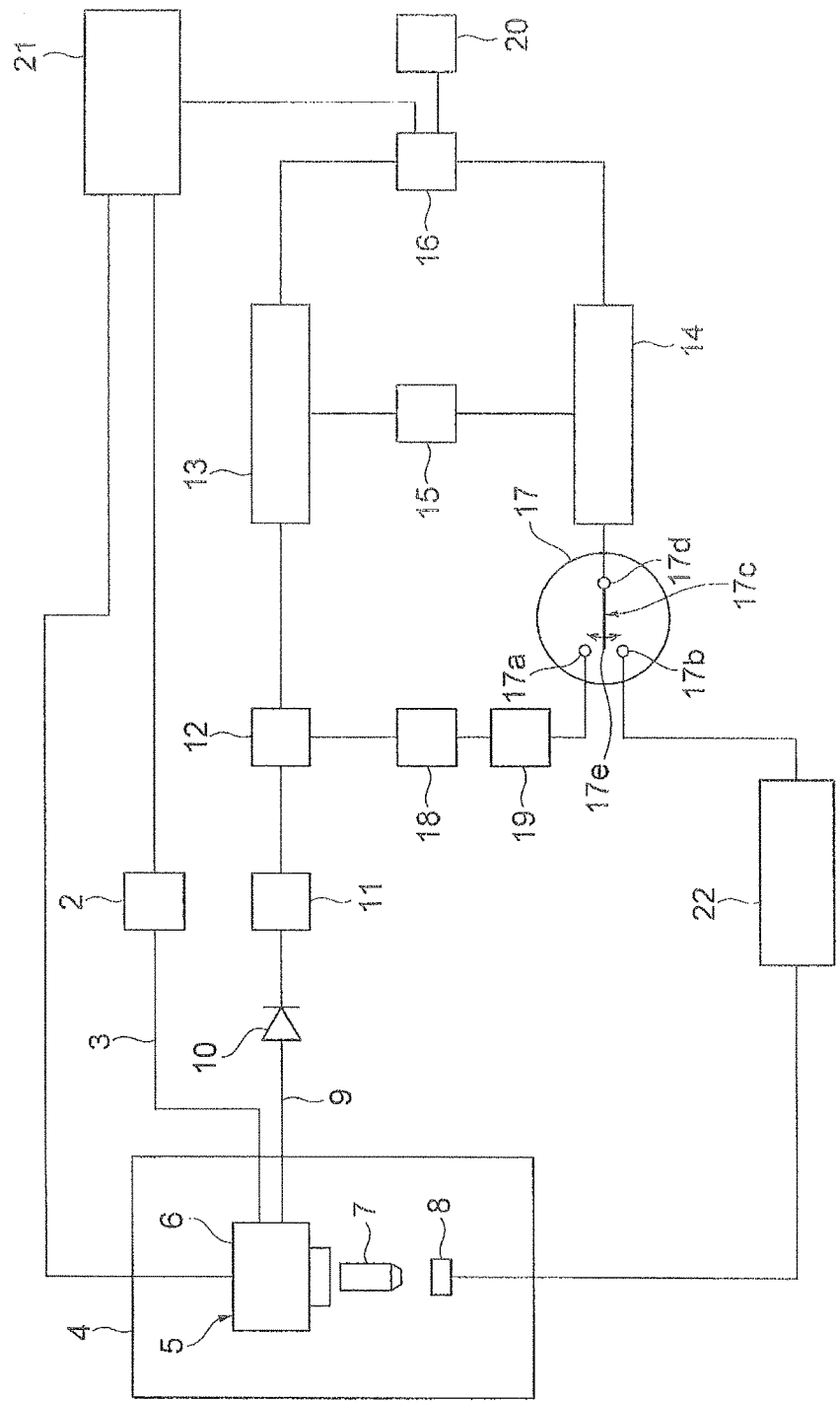
FIG. 1 is a configuration view of a semiconductor device inspection system of an embodiment of the present invention.

Hereinafter, an embodiment of the present invention will be described in detail with reference to the accompanying drawings. Further, the same or corresponding portions of the drawings are designated by the same reference numerals, and overlapping description thereof will be omitted.

As shown in FIG. 1, a semiconductor device inspection system 1 is a device for inspecting a semiconductor device 8, for example, specifying a place in which an abnormality occurs in the semiconductor device 8 serving as a device under test (DUT), and so on. As the semiconductor device 8, there are provided an integrated circuit having a PN junction such as a transistor or the like (for example, a small scale integrated (SSI) circuit, a medium scale integrated (MSI) circuit, a large scale integrated (LSI) circuit, a very large scale integrated (VLSI) circuit, an ultra large scale integrated (ULSI) circuit, and a giga scale integrated (GSI) circuit), a MOS transistor for large current/high pressure, a bipolar transistor, and so on. In addition, the semiconductor device 8 may be a semiconductor device in which modulation is applied to a substrate by heat.

The semiconductor device inspection system includes a laser light source (a light generating unit) 2. The laser light source 2 is operated by a first power supply (not shown), and emits light irradiated to the semiconductor device 8. The light emitted from the laser light source 2 is optically guided to a scan optical system 5 via a polarization preservation single mode optical fiber 3 for probe light. The scan optical system 5 has a scan head 6 and a lens system 7. Accordingly, the image of the light optically guided to the scan optical system 5 is formed at a predetermined position of the semiconductor device 8, and a radiation region of the light is two-dimensionally scanned to the semiconductor device 8. Further, the scan optical system 5 and the semiconductor device 8 are disposed in a black box 4.

The light reflected by the semiconductor device 8 when the light emitted from the laser light source 2 is irradiated to the semiconductor device 8 is optically guided to an optical sensor (a light detection unit) 10 via an optical fiber 9 for optical feedback. The optical sensor 10 is operated by a second power supply (not shown) installed separately from the first power supply (not shown), and detects the reflected light to output a detection signal. The detection signal output from the optical sensor 10 is output to a branch circuit 12 via an amplifier 11. The branch circuit 12 branches the detection signal and outputs detection signals. One of the branched detection signals is input to a spectrum analyzer (a first electricity measurement unit/a first spectrum analysis unit/a first spectrum analyzer) 13, and the other branched detection signal is input to a spectrum analyzer (a second electricity measurement unit/a second spectrum analysis unit/a second spectrum analyzer) 14 via an attenuator 18, an amplifier 19, and a switching unit 17. Further, the spectrum analysis unit is an electricity measurement means configured to measure amplitude of each component of a signal of a complex wave, such as a spectrum analyzer or the like.

The spectrum analyzers 13 and 14 are electrically coupled to each other via a signal synchronization unit 15. In addition, the spectrum analyzers 13 and 14 are electrically coupled to an output signal processing unit 16. The spectrum analyzers 13 and 14 generate a signal based on the input electrical signal (to be described in detail below), and the signal is input to the output signal processing unit 16. The output signal processing unit 16 generates an analysis signal based on the signal input by the spectrum analyzers 13 and 14, forms a semiconductor device image based on the analysis signal, and displays the semiconductor device image on a display unit 20.

A laser scan controller 21 is electrically coupled to the output signal processing unit 16. The laser scan controller 21 controls the laser light source 2 and the scan optical system 5. A tester unit (an operating signal application unit) 22 including a tester, a pulse generator and a power supply is electrically coupled to the spectrum analyzers 13 and 14. The tester unit 22 applies an operating signal (a test pattern) having a predetermined modulation frequency to the semiconductor device 8. Accordingly, the semiconductor device 8 is operated upon inspection.

Next, the switching unit 17, the attenuator 18, and the amplifier 19 will be described in detail. The switching unit 17 has a function of switching the signal input to the spectrum analyzer 14. The switching unit 17 has a detection signal terminal (a first signal terminal) 17a electrically coupled to the optical sensor 10, an operating signal terminal (a second signal terminal) 17b electrically coupled to the tester unit 22, and a connection section 17c having one end 17d electrically coupled to the spectrum analyzer 14. Switching of the signal input to the spectrum analyzer 14 by the switching unit 17 is performed by connecting the other end 17e of the connection section 17c to either the detection signal terminal 17a or the operating signal terminal 17b. That is, when the other end 17e is connected to the detection signal terminal 17a, the detection signal branched by the branch circuit 12 is input to the spectrum analyzer 14, and when the other end 17e is connected to the operating signal terminal 17b, the operating signal output from the tester unit 22 is input to the spectrum analyzer 14. Further, the amplifier 19 may be connected to the branch circuit 12, and the attenuator 18 may be connected to the detection signal terminal 17a of the switching unit 17.

The attenuator 18 and the amplifier 19 are installed between the spectrum analyzer 13 and the detection signal terminal 17a. The attenuator 18 has a function as a signal attenuation unit. The attenuator 18 attenuates electrical signals of the detection signal flowing from the optical sensor 10 toward the detection signal terminal 17a, the reflected signal flowing backward from the detection signal terminal 17a toward the spectrum analyzer 13, and the crosstalk signal flowing from the detection signal terminal 17a toward the spectrum analyzer 13. Here, the reflected signal flowing backward from the detection signal terminal 17a toward the spectrum analyzer 13 is a signal, for example, reflected by the detection signal terminal 17a of the switching unit 17 flowing backward toward the spectrum analyzer 13 among the detection signals flowing from the branch circuit 12 toward the detection signal terminal 17a when the other end 17e of the switching unit 17 is connected to the operating signal terminal 17b. In addition, the crosstalk signal flowing from the detection signal terminal 17a toward the spectrum analyzer 13 is a signal flowing toward the spectrum analyzer 13 generated as the operating signal flowing from the operating signal terminal 17b toward the spectrum analyzer 14 is leaked (turned around and cut into) due to an electrical action at the detection signal terminal 17a (or a wiring), which is not connected, in a state in which the other end 17e of the switching unit 17 is connected to the operating signal terminal 17b.

The amplifier 19 amplifies the electrical signal flowing from the light detection unit 10 toward the detection signal terminal 17a at a predetermined amplification rate, and attenuates the electrical signal flowing from the detection signal terminal 17a toward the spectrum analyzer 13. Accordingly, the amplifier 19 has both of a function as the signal amplification unit and a function as the signal attenuation unit. Accordingly, the amplifier 19 is set to amplify the detection signal flowing from the optical sensor 10 toward the detection signal terminal 17a via the attenuator 18. That is, the detection signal output from the optical sensor 10 is attenuated once by the attenuator 18, and then amplified to be equal to intensity before attenuation by the amplifier 19. In addition, the amplifier 19 is set to attenuate the reflected signal and the crosstalk signal flowing from the detection signal terminal 17a toward the spectrum analyzer 13 without amplification. An isolation amplifier, a buffer amplifier, or the like may be used as the above-mentioned the amplifier 19. In addition, the amplifier 19 may be configured to switch an amplification rate of the signal. In this case, an amplifier control unit (not shown) configured to control an amplification rate of the amplifier 19 is further provided, and the amplification rate with respect to the input signal is switched by the amplifier control unit (not shown). Accordingly, the amplifier 19 amplifies the electrical signal flowing from the light detection unit 10 toward the detection signal terminal 17a at a predetermined amplification rate, and amplifies the electrical signal flowing from the detection signal terminal 17a toward the spectrum analyzer 13 without amplification or at a low amplification rate.

Next, the spectrum analyzers 13 and 14, the signal synchronization unit 15 and the output signal processing unit 16 will be described in detail. A detection signal is input to the spectrum analyzer 13. In addition, a detection signal and an operating signal are selectively input to the spectrum analyzer 14. Specifically, when the other end 17e is connected to the detection signal terminal 17a, the detection signal detected by the optical sensor 10 is input to the spectrum analyzers 13 and 14. In this case, the output signal processing unit 16 sets a measurement frequency band FR1 with respect to the detection signal input to the spectrum analyzer 13 and a measurement frequency band FR2 with respect to the detection signal input to the spectrum analyzer 14. The spectrum analyzer 13 inputs the signal generated from the detection signal in the measurement frequency band FR1 to the output signal processing unit 16. In addition, the spectrum analyzer 14 inputs the signal generated from the detection signal in the measurement frequency band FR2 to the output signal processing unit 16. Then, the output signal processing unit 16 acquires an analysis signal by calculating a difference between the signals input from the spectrum analyzers 13 and 14.

In addition, when the other end 17e of the switching unit 17 is connected to the operating signal terminal 17b, the detection signal detected by the optical sensor 10 is input to the spectrum analyzer 13, and the operating signal applied to the semiconductor device 8 by the tester unit 22 or a signal that is an integer times the repetition frequency of the operating signal is input to the spectrum analyzer 14 as a reference signal. The spectrum analyzer 13 extracts a signal having a predetermined frequency from the detection signal and inputs the signal to the output signal processing unit 16. The spectrum analyzer 14 extracts the signal having the frequency of the reference signal and inputs the signal to the output signal processing unit 16. Then, the output signal processing unit 16 calculates a phase difference between the signal input by the spectrum analyzer 13 and the signal input by the spectrum analyzer 14, and makes a phase image based on the phase difference. On the assumption that the phase difference is calculated, synchronization of the frequency and the phase of the base signal that operates the spectrum analyzer 13 with the frequency and the phase of the base signal that operates the spectrum analyzer 14 is controlled by the signal synchronization unit 15.

Next, two measurement techniques (first and second measurement techniques) using the semiconductor device inspection system 1 will be described. The first measurement technique is a technique of connecting the other end 17e to the detection signal terminal 17a to specify an abnormal frequency and then connecting the other end 17e to the operating signal terminal 17b to specify a portion in which a failure occurs and a cause of the failure, In the first measurement technique, first, the other end 17e of the switching unit 17 is connected to the detection signal terminal 17a. Here, the detection signals detected in the optical sensor 10 are input to the spectrum analyzers 13 and 14. Further, the detection signals input to the spectrum analyzers 13 and 14 come from signals having a plurality of frequencies. Then, with respect to the output signal processing unit 16, the spectrum analyzer 13 is set to extract and output the signal of the measurement frequency band FR1 and the spectrum analyzer 14 is set to extract and output the signal of the measurement frequency band FR2. Further, the measurement frequency band FR1 and the measurement frequency band FR2 are different frequency bands.

Figure 2:
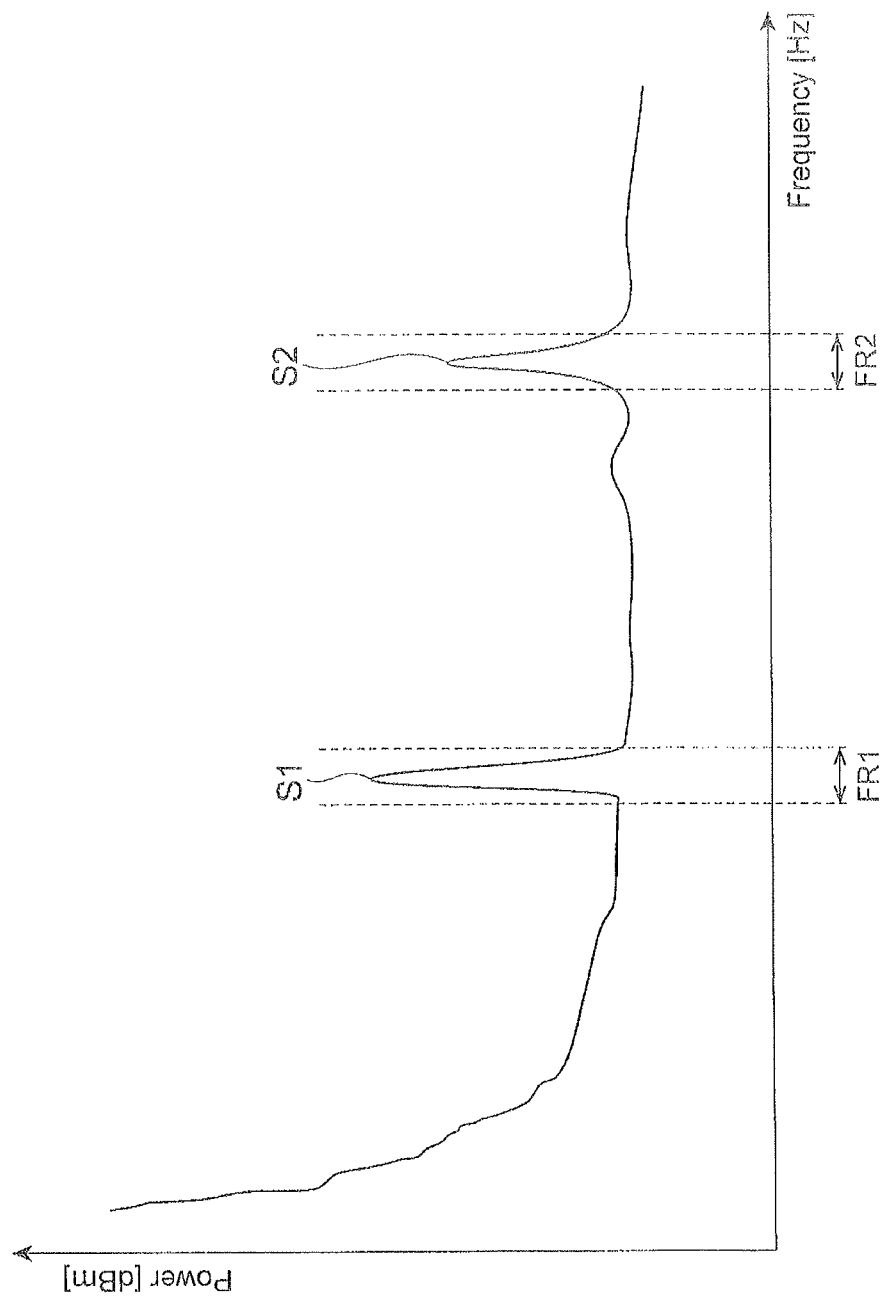
FIG. 2 is a graph showing a setting example of a frequency band in the semiconductor device inspection system of FIG. 1.

Setting of the above-mentioned output signal processing unit 16 will be described. For example, when the tester unit 22 applies the first operating signal having a first modulation frequency and a second operating signal having a second modulation frequency different from the first modulation frequency to the semiconductor device 8, in order to simultaneously observe modulations by these signals, the output signal processing unit 16 sets the measurement frequency band FR1 and the measurement frequency band FR2 based on the first modulation frequency of the first operating signal and the second modulation frequency of the second operating signal. That is, the measurement frequency band FR1 is set to include a frequency N times (N is a natural number) the first modulation frequency of the first operating signal, and the measurement frequency band FR2 is set to include a frequency N times (N is a natural number) the second modulation frequency of the second operating signal. Accordingly, as shown in FIG. 2, an analysis signal from which coherent noises or the like of the semiconductor device inspection system are removed in the measurement frequency bands FR1 and FR2 can be acquired from a difference between a measurement signal S1 based on the measurement frequency band FR1 generated by the spectrum analyzer 13 and a measurement signal S2 based on the measurement frequency band FR2 generated by the spectrum analyzer 14. The analysis signal has an amplitude image displayed on the display unit 20 by the output signal processing unit 16.

Then, the amplitude image of the analysis signal displayed on the display unit 20 is confirmed, and the frequency that forms an image different from a conventional amplitude image is specified as a frequency (an abnormal frequency) including a signal caused by a failure. Further, confirmation of the amplitude image of the analysis signal is performed by repeatedly changing settings of the measurement frequency bands FR1 and FR2 until the abnormal frequency is acquired.

Then, when the abnormal frequency is specified, the other end 17e of the switching unit 17 is switched from a state in which it is connected to the detection signal terminal 17a to a state in which it is connected to the operating signal terminal 17b. Here, the detection signal detected by the optical sensor 10 is input to the spectrum analyzer 13, and the operating signal applied to the semiconductor device 8 by the tester unit 22 is input to the spectrum analyzer 14. The detection signal having the above-mentioned abnormal frequency is input to the spectrum analyzer 13. Further, according to the setting of the signal synchronization unit 15, the frequency and the phase of the base signal that operates the spectrum analyzer 13 are controlled to be synchronized with the frequency and the phase of the base signal that operates the spectrum analyzer 14.

The signals output from the spectrum analyzers 13 and 14 are input to the output signal processing unit 16. Then, the phase difference between the signals output from the spectrum analyzers 13 and 14 is calculated by the output signal processing unit 16, and the phase image based on the phase difference is displayed on the display unit 20. Such a phase image changes the radiation region of the light in the semiconductor device 8 optically guided to the scan optical system 5, and is made in each radiation region. The phase image is displayed in a color based on the phase difference. By understanding what color corresponds to the phase difference between the signals output from the spectrum analyzers 13 and 14 of each radiation region, a place at which the color diverges from the appropriate color (is not an ideal phase difference) can be specified as a portion of the semiconductor device 8 in which a failure occurs. In addition, the cause of the failure can be specified according to a degree of divergence from the appropriate color or whether the color is a specific color. Further, the cause of the failure is, for example, breakage of a wiring between elements of the semiconductor device 8, presence of a high resistance portion, or the like.

Next, the second measurement technique will be described. The second measurement technique is a technique of acquiring a signal by connecting the other end 17e to the detection signal terminal 17a and removing inherent noise of the semiconductor device inspection system, after connecting the other end 17e to the operating signal terminal 17b and specifying the portion in which the failure occurs and the cause of the failure from the phase difference.

In the second measurement technique, first, the other end 17e of the switching unit 17 is connected to the operating signal terminal 17b. Here, the detection signal detected by the optical sensor 10 is input to the spectrum analyzer 13, and the operating signal applied to the semiconductor device 8 by the tester unit 22 is applied to the spectrum analyzer 14. With respect to the output signal processing unit 16, the spectrum analyzer 13 is set to extract and output the signal having a predetermined frequency from the detection signal, and the spectrum analyzer 14 is set to extract and output the signal of the frequency of the operating signal.

The signals output from the spectrum analyzers 13 and 14 are input to the output signal processing unit 16. Then, the phase difference of the signals output from the spectrum analyzers 13 and 14 is calculated by the output signal processing unit 16, and the phase image is displayed on the display unit 20 based on the phase difference. Such a phase image changes the radiation region of the light in the semiconductor device 8 optically guided to the scan optical system 5, and is made in each radiation region. The phase image is displayed in a color based on the phase difference. When the portion in which the failure occurs is specified from the phase image, the scan optical system 5 is adjusted such that the portion in which the failure occurs becomes the radiation region of the light.

Figure 3:
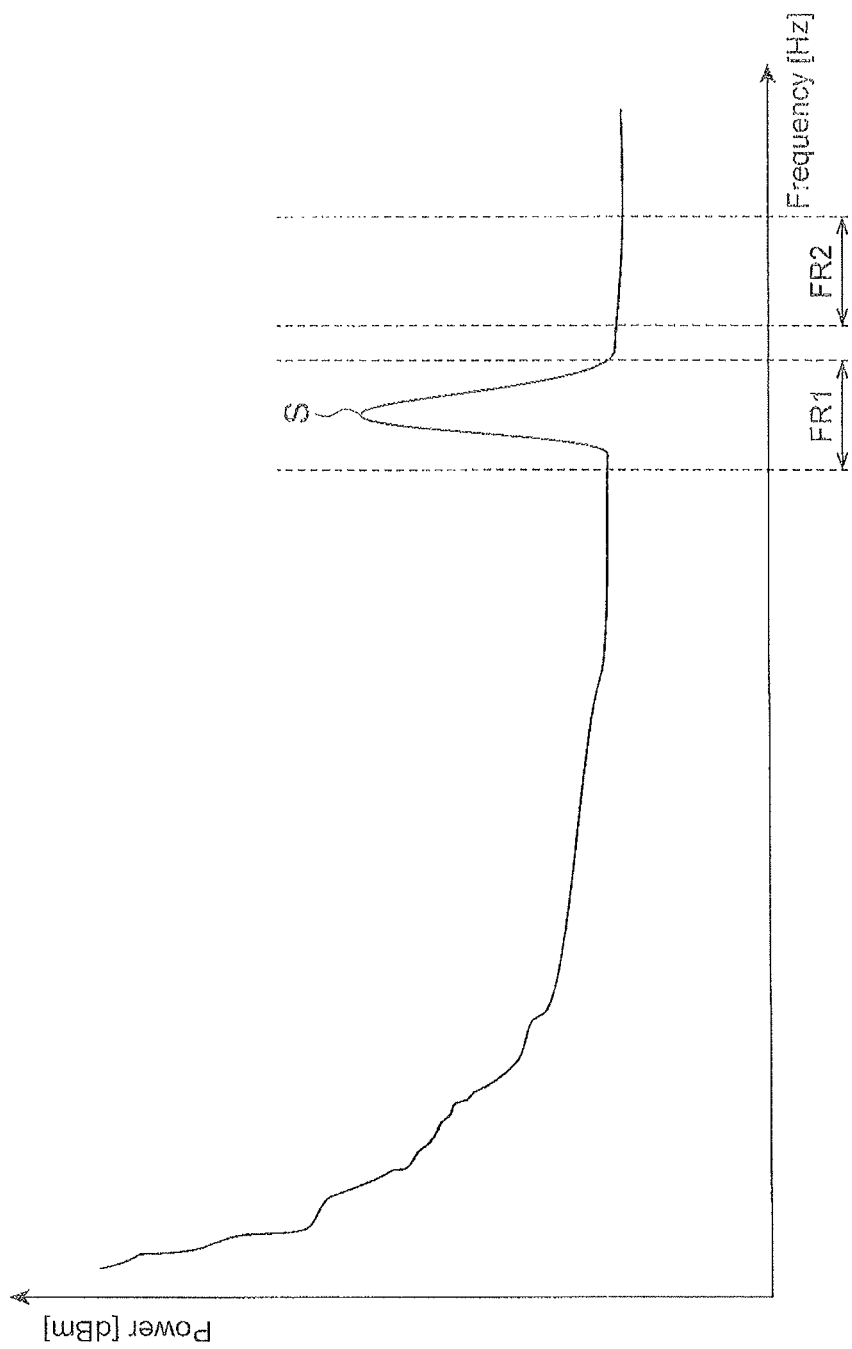
FIG. 3 is a graph showing the setting example of the frequency band in the semiconductor device inspection system of FIG. 1.

Then, the other end 17e of the switching unit 17 is switched from a state in which it is connected to the operating signal terminal 17b to a state in which it is connected to the detection signal terminal 17a. Here, the detection signals detected by the optical sensors 10 are input to the spectrum analyzers 13 and 14. Further, the signals from the optical sensors 10 are constituted by the signals having a plurality of frequencies. Then, with respect to the output signal processing unit 16, as shown in FIG. 3, the spectrum analyzer 13 is set to extract and output the signal of a predetermined frequency band (a frequency band for measurement) FR1, and the spectrum analyzer 14 is set to extract and output the signal of the frequency band (the frequency band for reference) FR2 having a level obtained by adding a frequency hand having no frequency dependency in the inherent noise of the semiconductor device inspection system or less.

Then, as the output signal processing unit 16 receives a difference between the signals input from the spectrum analyzer 13 and the spectrum analyzer 14, a signal (an analysis signal) from which white noise is removed can be acquired. As the analysis signal is used, high precision of the measurement result can be achieved.

As described above, in the semiconductor device inspection system 1, a semiconductor device inspection method includes a light generation step of generating light irradiated to the semiconductor device 8, a light detection step of detecting the light reflected by the semiconductor device 8 when the light generated in the light generation step is irradiated to the semiconductor device 8 and outputting the detection signal, an operating signal application step of applying an operating signal to operate the semiconductor device 8 to the semiconductor device 8, a first measurement step of inputting the detection signal to the spectrum analyzer 13, and a second measurement step of selectively inputting the detection signal and the operating signal to the spectrum analyzer 14.

In addition, as described above, the second measurement step may be a technique of inputting the operating signal to the spectrum analyzer 14 after the detection signal is input to the spectrum analyzer 14, and a technique of inputting the detection signal to the spectrum analyzer 14 after the operating signal is input to the spectrum analyzer 14.

In this way, in the semiconductor device inspection system 1, when the switching unit 17 sets an access point of the other end 17e as the detection signal terminal 17a, the amplitudes having two frequencies can be simultaneously measured by the spectrum analyzers 13 and 14. That is, inspection of the semiconductor device 8 is efficiently performed. In addition, when the switching unit 17 sets the access point of the other end 17e as the operating signal terminal 17b, since the detection signal is input to the spectrum analyzer 13 and the operating signal is input to the spectrum analyzer 14, the phase difference can be calculated from the phase of the detection signal and the phase of the operating signal, and the portion in which the failure occurs and the cause of the failure can be specified according to the phase difference. That is, inspection of the semiconductor device 8 can be precisely performed. Accordingly, according to the semiconductor device inspection system 1, inspection of the semiconductor device 8 can be efficiently and precisely performed.

In addition, when the switching unit 17 connects the other end 17e to the operating signal terminal 17b, as the signal synchronization unit 15 configured to synchronize the frequency and the phase of the base signal that operates the spectrum analyzer 13 with the frequency and the phase of the base signal that operates the spectrum analyzer 14, overlapping of the phase differences due to the error of the reference frequency between the spectrum analyzers 13 and 14 is prevented, and the phase difference between the detection signal and the operating signal can be more precisely calculated.

In addition, when the switching unit 17 installed between the spectrum analyzer 13 and the detection signal terminal connects the other end 17e connected to the detection signal terminal to the operating signal terminal 17b, as a signal attenuation unit configured to attenuate an electrical signal flowing in a direction from the detection signal terminal toward the spectrum analyzer 13 is further provided, when the switching unit 17 switches the connection of the other end 17e from the detection signal terminal 17a to the operating signal terminal 17b, the detection signal flowing backward from the detection signal terminal 17a toward the spectrum analyzer 13 and the operating signal flowing from the detection signal terminal 17a toward the spectrum analyzer 13 can be appropriately attenuated. Accordingly, the noise signal can be input to the spectrum analyzer 13, and the phase difference between the detection signal and the operating signal can be more securely calculated.

While the embodiment of the present invention has been described above, the present invention is not limited to the above-mentioned embodiment. For example, the light generating unit configured to generate the light irradiated to the semiconductor device 8 is not limited to the laser light source 2 but may be applied to another light source such as a super luminescent diode or the like. In addition, instead of the electrical signal, heat may be applied to the semiconductor device 8. In addition, the first electricity measurement unit and the second electricity measurement unit are not limited to the spectrum analyzer such as spectrum analyzers or the like but may be various electricity measurement instruments (or an apparatus having these functions) such as a lock-in amplifier, an oscilloscope, or the like. In addition, these electricity measurement instruments may be combined, and for example, the spectrum analyzer may be employed as the first electricity measurement unit and the lock-in amplifier may be employed as the second electricity measurement unit. Further, a spectrum analyzer including a plurality of spectrum analysis units may be used. Such a spectrum analyzer includes a first channel configured to input a signal to a first electricity measurement unit corresponding to the spectrum analyzer 13, and a second channel configured to input a signal to a second electricity measurement unit corresponding to the spectrum analyzer 14. The first channel is electrically coupled to the branch circuit 12, and the second channel is electrically coupled to the other end 17d of the switching unit 17.

Figure 4:
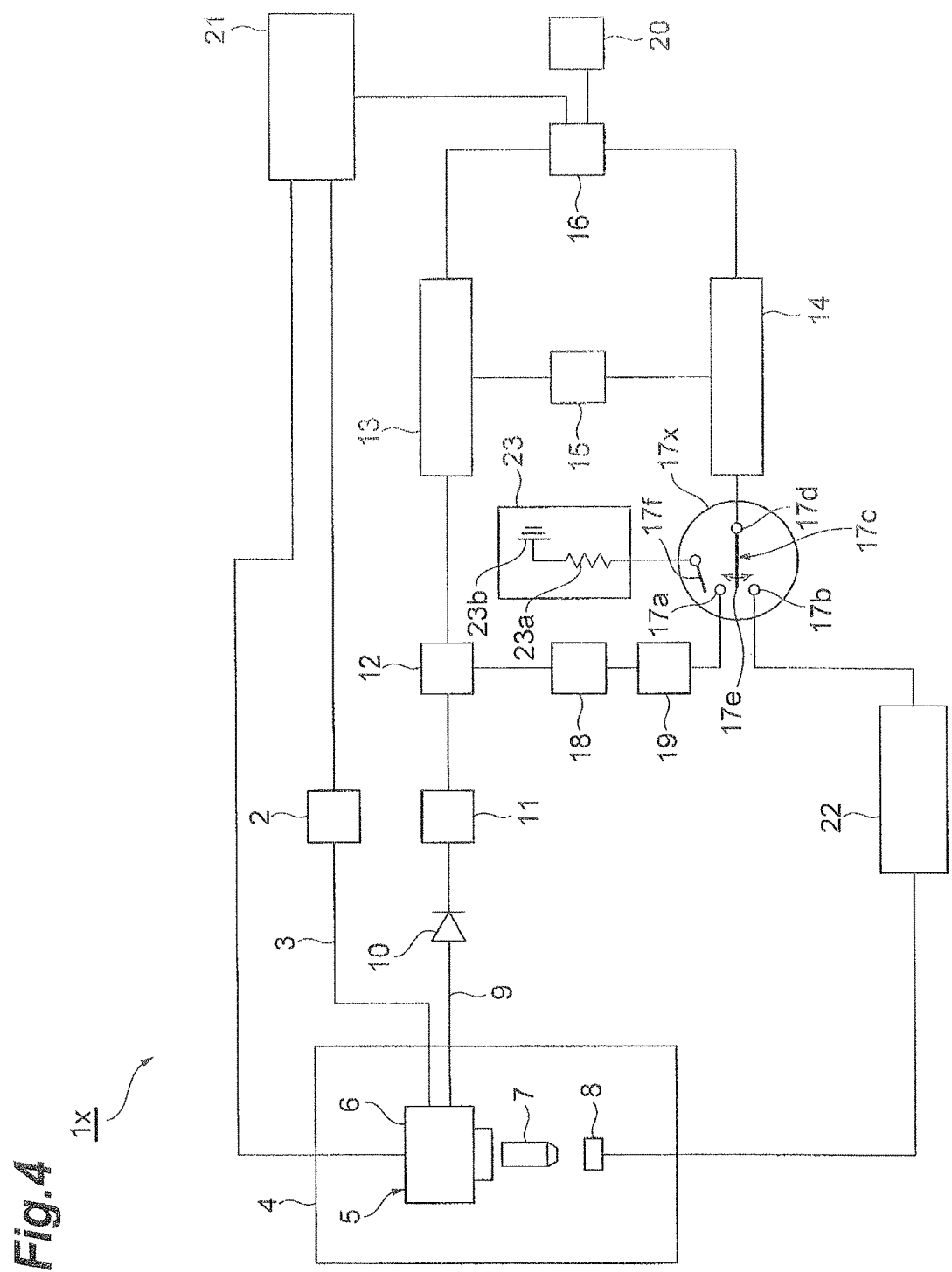
FIG. 4 is a configuration view of a semiconductor device inspection system of another embodiment of the present invention.

In addition, like a semiconductor device inspection system 1x as shown in FIG. 4, when a signal attenuation mechanism 23 having an electrical resistor 23a connected to a ground terminal 23b is provided as the signal attenuation unit, an attenuation switching unit 17f having one end connected to the electrical resistor 23a is provided, and the other end 17e of the switching unit 17 connected to the detection signal terminal 17a is connected to the operating signal terminal 17b, an end section of the switching unit 17 that is not connected to the electrical resistor 23a of the attenuation switching unit 17f may be connected to the detection signal terminal 17a. According to this configuration, when the switching unit 17 switches the connection of the other end 17e from the detection signal terminal 17a to the operating signal terminal 17b, since the attenuation switching unit 17f is connected to the detection signal terminal 17a, the electrical signal flowing from the detection signal terminal 17a to the spectrum analyzer 13 is output to the ground. Accordingly, the electrical signal flowing from the detection signal terminal 17a toward the spectrum analyzer 13 can be appropriately attenuated. Further, the signal attenuation unit constituted by the attenuator 18 and the amplifier 19 may be installed between the detection signal terminal 17a and the branch circuit 12.

Figure 5:
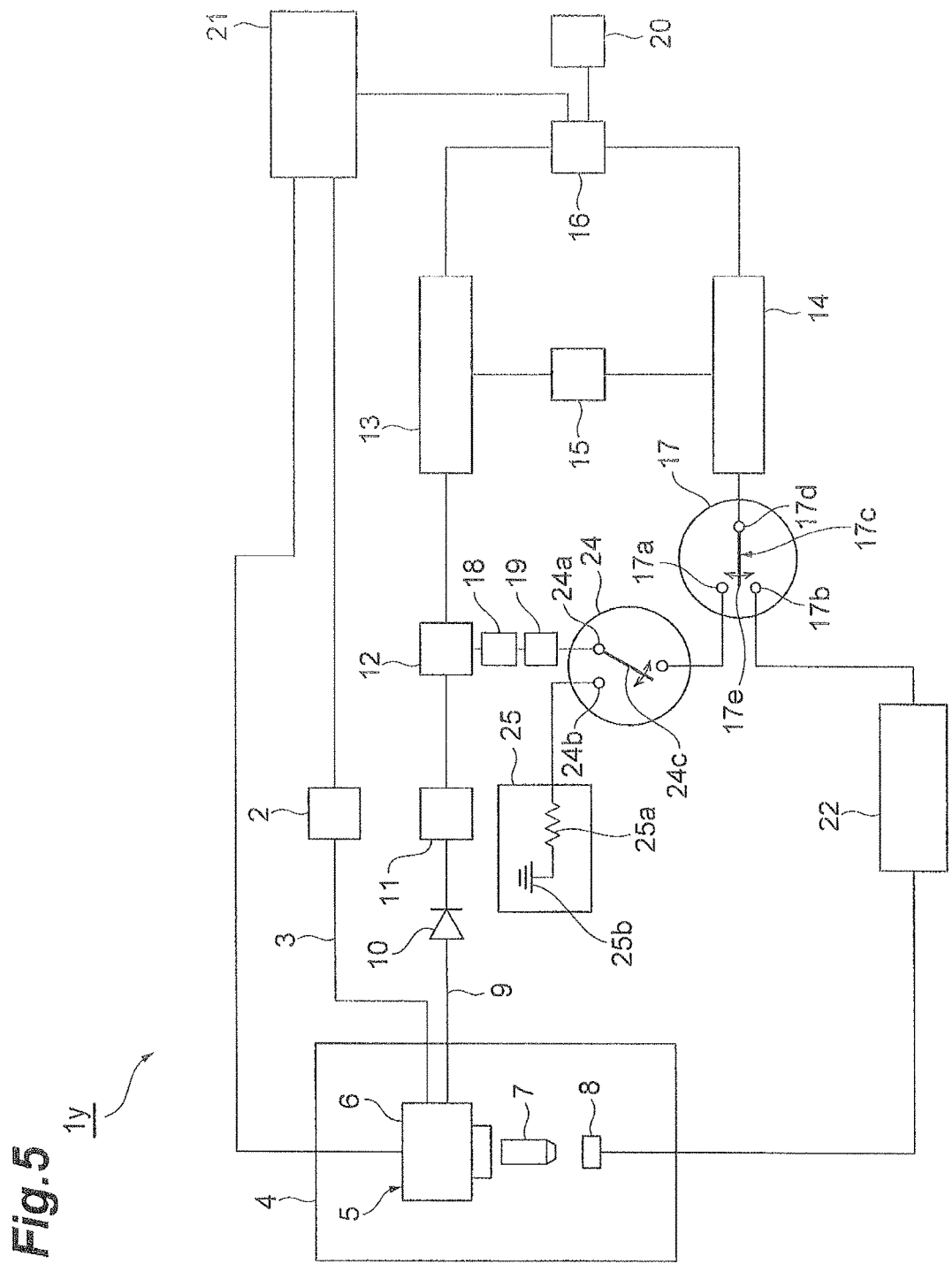
FIG. 5 is a configuration view of a semiconductor device inspection system of another embodiment of the present invention.

In addition, like a semiconductor device inspection system 1y shown in FIG. 5, a signal attenuation mechanism 25 having an electrical resistor 25a connected to a ground terminal 25b may be provided as the signal attenuation unit, and an intermediate switching unit 24 constituted by a branch circuit terminal (a fourth signal terminal) 24a electrically coupled to the branch circuit 12, an attenuation terminal (a third signal terminal) 24b electrically coupled to the electrical resistor 25a, and an intermediate connection section 24c through which the branch circuit terminal 24a is electrically coupled to the attenuation terminal 24b or one end is electrically coupled to the detection signal terminal 17a and can be connected to any of the other ends may be provided. According to the configuration, as the one end that electrically couples the intermediate connection section 24c to the detection signal terminal 17a is connected to the other end when the switching unit 17 connects the other end 17e to the detection signal terminal 17a and the intermediate connection section 24c is connected to the attenuation terminal 24b when the switching unit 17 switches the connection of the other end 17e from the detection signal terminal 17a to the operating signal terminal 17b, the electrical signal flowing from the branch circuit terminal 24a toward the spectrum analyzer 13 is output to the ground. Accordingly, the electrical signal flowing from the detection signal terminal 17a toward the spectrum analyzer 13 can be appropriately attenuated. Further, the signal attenuation unit constituted by the attenuator 18 and the amplifier 19 may be further provided between the branch circuit terminal 24a and the branch circuit 12.

REFERENCE SIGNS LIST 1, 1x, 1y . . . semiconductor device inspection system, 2 . . . laser light source (light generating unit), 8 . . . semiconductor device, 10 . . . optical sensor (light detection unit), 12 . . . branch circuit, 13 . . . spectrum analyzer (first electricity measurement unit, first spectrum analysis unit, first spectrum analyzer), 14 . . . spectrum analyzer (second electricity measurement unit, second spectrum analysis unit, second spectrum analyzer), 15 . . . signal synchronization unit, 16 . . . output signal processing unit, 17 . . . switching unit, 17a . . . detection signal terminal (first signal terminal), 17b . . . operating signal terminal (second signal terminal), 17c . . . connection section, 17d . . . one end, 17e . . . other end, 17f . . . attenuation switching unit, 18 . . . attenuator (signal attenuation unit/attenuator), 19 . . . amplifier (signal attenuation unit/amplifier), 20 . . . display unit, 22 . . . tester unit (operating signal application unit), 23a, 25a . . . electrical resistor, 23b, 25b . . . ground, 24a . . . branch circuit terminal (fourth signal terminal), 24b . . . attenuation terminal (third signal terminal), 24c . . . intermediate connection section

The invention claimed is:

1. A system for inspecting a semiconductor device serving as a device under test, the system comprising:
   a light source configured to generate light to be irradiated the semiconductor device;
   a light detector configured to detect the light reflected by the semiconductor device and output a detection signal;
   an operating signal application unit configured to apply the operating signal to the semiconductor device;
   a first electricity measurement unit electrically coupled to the light detector, to which the detection signal is input;
   a second electricity measurement unit to which the detection signal and a reference signal are selectively input; and
   a switching unit having a first signal terminal electrically coupled to the light detector, a second signal terminal electrically coupled to the operating signal application unit, and a connection section having one end electrically coupled to the second electricity measurement unit,
   wherein the switching unit inputs the detection signal to the second electricity measurement unit by connecting the other end of the connection section to the first signal terminal, and inputs the reference signal to the second electricity measurement unit by connecting the other end of the connection section to the second signal terminal.

2. The system according to claim 1, further comprising a signal attenuation unit installed between the first electricity measurement unit and the first signal terminal and configured to attenuate an electrical signal flowing in a direction from the first signal terminal toward the first electricity measurement unit.

3. The system according to claim 2, wherein the signal attenuation unit comprises an amplifier configured to amplify an electrical signal from the light detector toward the first signal terminal, and attenuate an electrical signal from the first signal terminal toward the first electricity measurement unit.

4. The system according to claim 2, wherein the signal attenuation unit comprises an amplifier configured to amplify an electrical signal from the light detector toward the first signal terminal, and an attenuator configured to attenuate an electrical signal from the light detector toward the first signal terminal and an electrical signal from the first signal terminal toward the first electricity measurement unit.

5. The system according to claim 2, wherein the signal attenuation unit comprises an electrical resistor electrically coupled to the ground,
the switching unit comprises an attenuation switching unit electrically coupled to the electrical resistor, and
the switching unit electrically couples the attenuation switching unit to the first signal terminal when the other end of the connection section is connected to the second signal terminal.

6. The system according to claim 2, wherein the signal attenuation unit comprises an electrical resistor electrically coupled to the ground,
the switching unit further has a third signal terminal electrically coupled to the electrical resistor, a fourth signal terminal electrically coupled to the light detector, and an intermediate connection section having one end electrically coupled to the first signal terminal, and
the switching unit connects the intermediate connection section to the fourth signal terminal when the other end of the connection section is connected to the first signal terminal, and connects the intermediate connection section to the third signal terminal when the other end of the connection section is connected to the second signal terminal.

7. The system according to claim 1, wherein the first electricity measurement unit and the second electricity measurement unit comprise a first spectrum analyzer and a second spectrum analyzer for measuring amplitudes of components of a complex wave.

8. The system according to claim 7, further comprising a signal synchronization unit configured to synchronize a frequency and a phase of a base signal that operates the first spectrum analyzer with a frequency and a phase of a base signal that operates the second spectrum analyzer when the switching unit connects the other end to the second signal terminal.

9. The system according to claim 1, wherein the first electricity measurement unit comprises a spectrum analyzer configured to measure amplitudes of components of a complex wave, and the second electricity measurement unit comprises a lock-in amplifier.

10. A method for inspecting a semiconductor device serving as a device under test, the method comprising:
generating light irradiated to the semiconductor device;
detecting the light reflected by the semiconductor device and outputting the detection signal;
applying an operating signal to the semiconductor device;
inputting the detection signal to a first electricity measurement unit; and
selectively inputting the detection signal and a reference signal to a second electricity measurement unit.

11. The method according to claim 10, wherein selectively inputting comprises the reference signal is input to the second electricity measurement unit after the detection signal is input to the second electricity measurement unit.

12. The method according to claim 10, wherein selectively inputting comprises the detection signal is input to the second electricity measurement unit after the reference signal is input to the second electricity measurement unit.

* * * * *